United States Patent [19]

Wright et al.

[11] Patent Number: 4,512,853

[45] Date of Patent: Apr. 23, 1985

[54] METHOD OF MONITORING PH

[75] Inventor: David B. Wright; Brian D. Sharpe, both of Cleveland, Tenn.

[73] Assignee: Olin Corporation, Cheshire, Conn.

[21] Appl. No.: 495,219

[22] Filed: May 17, 1983

Related U.S. Application Data

[63] Continuation-in-part of Ser. No. 377,756, May 18, 1982.

[51] Int. Cl.³ .......................................... G01N 27/46
[52] U.S. Cl. .................................. 204/1 T; 204/400; 204/409; 204/420; 204/433; 204/435
[58] Field of Search ............. 204/1 T, 1 H, 400, 409, 204/420, 433, 435

[56] References Cited

U.S. PATENT DOCUMENTS

| | | | |
|---|---|---|---|
| 2,563,062 | 8/1951 | Perley | 204/195 G |
| 3,661,724 | 5/1972 | Strickler | 204/409 |
| 3,709,796 | 1/1973 | King et al. | 204/195 R |
| 3,718,556 | 2/1973 | Rohrback | 204/433 |
| 4,105,507 | 8/1978 | Von Krusenstierna | 204/15 |
| 4,115,235 | 9/1978 | Capone | 204/409 |
| 4,128,468 | 12/1978 | Bukamier | 204/195 |
| 4,163,698 | 8/1979 | Kuo et al. | 204/435 |
| 4,177,126 | 12/1979 | Imaki et al. | 204/195 F |
| 4,360,415 | 11/1982 | Brezinski | 204/195 F |

OTHER PUBLICATIONS

Advertising Brochure for Sensor Assembly.

Primary Examiner—T. Tung
Attorney, Agent, or Firm—Ralph D'Alessandro; Donald F. Clements; Thomas P. O'Day

[57] ABSTRACT

A method of electrometrically monitoring the pH of an electrolyte in an electrolytic cell with a pH sensor having a reference electrode with a porous membrane is provided by placing the pH sensor in the electrolyte flow stream, floating the reference electrode at the cell potential, and monitoring the pH sensor readings via potential measuring apparatus.

12 Claims, 1 Drawing Figure

METHOD OF MONITORING PH

BACKGROUND OF THE INVENTION

This is a continuation-in-part application of Patent Application Ser. No. 337,756 filed May 13, 1982.

This invention relates generally to electrolytic cells and more particularly to a method of electrometrically monitoring the pH of electrolyte in the electrolytic cell.

Electrometric pH measurements are used today in many laboratory and commercial continuous process applications. Wide scale usage of such pH measurements is primarily due to the development of pH sensors that employ a glass electrode together with a second or reference electrode that is stable and able to produce a predictable potential compatible with the glass measuring electrode. It is desirable to monitor the pH of the electrolyte during the operation of an electrolytic cell, such as a chloralkali or a sodium chlorate electrolytic cell, to ensure cell performance is optimized.

The monitoring of electrolyte pH is especially significant in the relatively recently developed filter press membrane type of chloralkali electrolytic cell wherein an ion selective membrane is employed between adjacent anodes and cathodes. These membranes, such as the Flemion ® brand sold by Ashai Glass Company, or the Nafion ® brand sold by the E. I. DuPont de Nemours and Company, generally require the electrolyte with which they are in contact to be within a predetermined and relatively narrow pH range during cell operation. Should the pH of the electrolyte which is in contact with the membranes drop to too low a level, the membranes will tighten up and prevent the passage of sodium ions thereacross. In the instance of the Flemion membranes, the membranes can operate in a pH range of approximately 2.5 to about 4.5.

However, chlorine current efficiency with this type of membrane, for example, requires the electrolyte pH to be on the lower end of this scale. Without the addition of acid, filter press membrane chloralkali cells will operate normally between about 3.5 and about 4.5 pH. At this pH level the cell will buffer itself so it will not operate at the best efficiency. The chlorine current efficiency will be low if the electrolyte is at this level. This is evidenced by caustic in the cathode chamber crossing the membranes and reacting with the chlorine to reduce the amount of product chlorine available. It is, therefore, desirable to control the pH level through monitoring by the addition of acid to the salt brine.

Attempts to monitor the pH through the use of pH sensors or probes have encountered problems in the anolyte of filter press membrane type of electrolytic cells. Failure frequently occurs in the reference electrode that is a part of the pH probe because of chemical attack by the anolyte stream components of the reference electrolyte solutions in the pH sensor or probe, chemical attack of the porous plug or salt bridge material, or chemical attack of the pH sensitive glass used in the pH sensor or probe. An additional problem is encountered because of the stray currents that are sensed by the pH probe and which affect the accuracy of the readings.

These problems are solved in the method of the instant invention employing a reference electrode with a porous polytetrafluoroethylene membrane in a pH sensor, using a glass electrode, in the electrolyte of an electrochemical cell to electrometrically monitor the pH of the anolyte stream in a chloralkali electrolytic cell.

SUMMARY OF THE INVENTION

It is an object of the present invention to provide a method of employing an electrometric pH sensor with a reference electrode having a porous polytetrafluoroethylene membrane to monitor pH in the anolyte stream of a membrane electrolytic cell.

It is another object of the present invention to provide a simple and reliable method for obtaining continuous and reliable readings of the pH of an electrolyte in an electrolytic cell.

It is a feature of the present invention that the method employs a pH sensor with a reference electrode having a porous polytetrafluoroethylene membrane at a low point in the flow loop of the electrolyte stream to avoid asymmetry potential change or drift to ensure that the porous polytetrafluoroethylene membrane is always moist.

It is another feature of the method of the present invention that the pH sensor is left ungrounded so that the reference electrode varies electrically with the electrolytic cell potential of the anolyte stream without being influenced by stray currents.

It is still another feature of the method of the present invention that an acclimation period is employed to displace wetting solution in the pH sensor so that the cell electrolyte becomes the reference electrolyte and the reference potentials are established.

It is an advantage of the method of the present invention that reliable and continuous monitoring of the pH of an electrolyte in an electrochemical cell can be obtained.

It is another advantage of the method of the present invention that more reliable electrometric pH readings over an extended period of time are obtained because the electrolyte in the cell anolyte stream is the reference electrolyte in the pH sensor.

These and other objects, features, and advantages are provided in the method of electrometrically measuring the pH of the electrolyte in an electrolytic cell with a pH sensor having a reference electrode with a porous polytetrafluoroethylene membrane by placing the ungrounded pH sensor in the electrolyte flow stream and maintaining the reference electrode at the electrolytic cell potential with respect to some standard glass electrode potential.

BRIEF DESCRIPTION OF THE DRAWINGS

The advantages of this invention will become apparent upon consideration of the following detailed disclosure of the invention, especially when it is taken in conjunction with the following drawing wherein.

DETAILED DESCRIPTION OF THE PREFERRED EMBODIMENT

Figure 1:
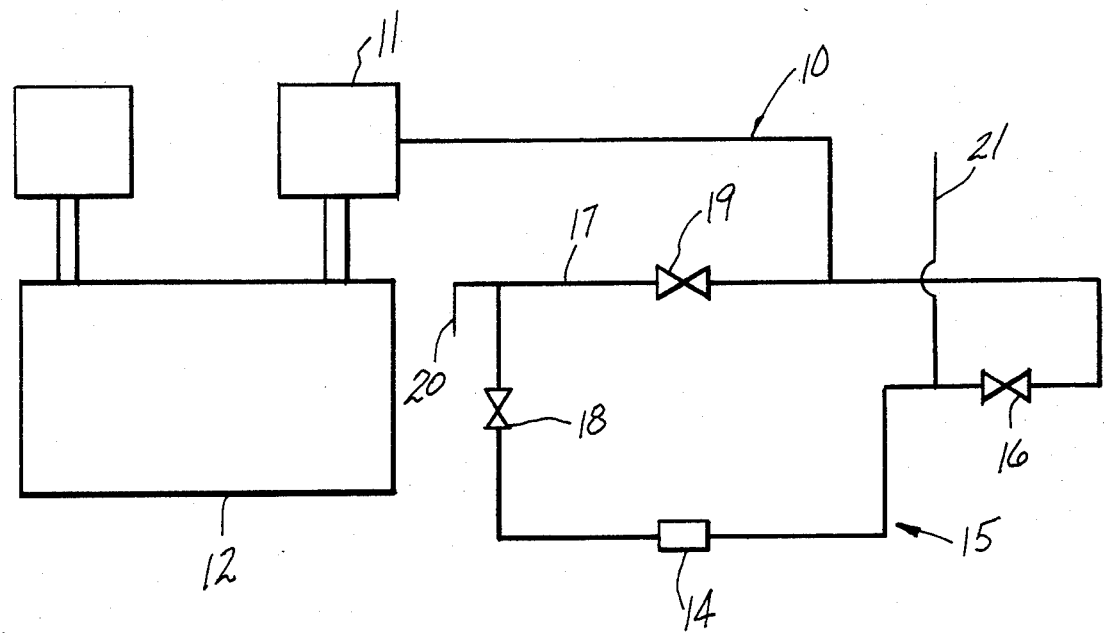
FIG. 1 is a diagrammatic illustration of a flow loop of any anolyte flow stream from an electrolytic cell.

The method of electrometrically monitoring the pH is discussed hereafter with reference to FIG. 1, wherein there is illustrated a flow loop, indicated generally by the numeral 10, of an anolyte flow stream from the anolyte disengager 11 of a diagramatically illustrated electrolytic cell 12. In a chloralkali electrolytic cell, such as a filter press membrane type of cell, the anolyte flow stream consists of spent brine that exits the anolyte gas-liquid disengager 11 through an appropriately sized conduit enroute to a brine resaturator (not shown). It is to be understood that the method of the instant invention, although discussed and exemplified in the context of a chloralkali electrolytic cell with external gas-liquid disengagers, such as a filter press membrane cell, could equally well be employed in any type of chloralkali cell, with or without external gas-liquid disengagers. Additionally the method of electrometrically monitoring the pH could also be applicable to chlorate production, potassium chloride/potassium hydroxide processes or other electrolytic processes where the pH sensor must be subjected to a harsh environment because of strong electrolytes.

The method of the instant invention in a chloralkali electrolytic cell employs an electrometric pH sensor 14 in the flow loop of the anolyte flow stream to monitor the pH of the brine or electrolyte. As can be seen in FIG. 1, the flow loop 10 employs a main loop, indicated by the numeral 15, within which the pH sensor 14 is emplaced. The pH sensor 14 is located at the lowest point or level of the main loop 15 so that the reference electrode, with its porous polytetrafluoroethylene membrane, may always be immersed in the electrolyte to maintain its moisture and avoid asymmetry potential drift problems. These asymmetry potential drift problems result when the pH sensor and its electrodes have been in dry storage for a period of time or are permitted to dry out because of interruptions in the operation of the cell. When this occurs and the pH sensor is then reimmersed in electrolyte, the pH readings generally tend to drift for predetermined periods of time, often as much as 24–48 hours, until a condition of full equilibrium is achieved. By employing the pH sensor, with its reference electrode and the porous polytetrafluoroethylene membrane therein, in the lowest portion of the main loop 15, any shut-down in the operation of the cell will not cause the pH sensor and its electrodes to dry out and affect the membrane and the reference electrode. Typical cell shut-downs are routinely scheduled, such as for maintenance, or can be the result of unexpected power outages.

The main loop 15 in FIG. 1 is isolatable from the by-pass flow path 17 of the flow loop 10 by a pair of shut-off valves, 16 and 18, respectively. These shut-off valves permit the flow of electrolyte, in this case spent brine, into the main loop 15 to be stopped should it be necessary to perform maintenance or remove the pH sensor 14. A third shut-off valve 19 is employed in the flow loop 10 to permit the flow of electrolyte or brine to follow its normal flow path and be forced through the main loop 15 when electrometric pH monitoring is desired. This is accomplished by closing the shut-off valve 19, thus forcing the electrolyte solution or brine to flow through the valve 16 via pH sensor 14 and the valve 18 before it continues into the main flow line 20 enroute to the brine resaturator (not shown). The shut-off valves 16, 18, and 19, may have check valves built in to prevent the back flow of brine therethrough. When it is desired to direct the spent brine in the anolyte flow stream into the main flow line 20 via the by-pass flow path 17 without passing through the main loop 15, the shut-off valves 16 and 18 are closed and shut-off valve 19 is opened.

A siphon break 21 is employed in the main loop 15 by use of a vent pipe, for example, that provides a vent to the chlorine header to permit a pressure slightly less than atmospheric pressure to be exerted on the electrolyte within the flow loop and prevent the electrolyte from being siphoned out of the main loop 15 and the pH sensor 14 during operation.

As shown, the pH sensor 14 is used to measure the anolyte or brine pH for an electrolytic cell, typically a filter press membrane chloralkali type of electrolytic cell. The pH sensor 14 is installed directly in the return line or anolyte effluent stream from the disengager 11 to the brine resaturator (not shown) where it can continuously monitor the brine pH. The pH sensor is allowed to electrically vary or fluctuate with the electrical potential of the anolyte stream so that the reference electrode is maintained at the electrolytic cell's anolyte stream potential. Ground loop circuits are avoided by not employing a reference electrode solution ground through the pH sensor to the pH potentiometer or pH measuring instrument so that inaccurate readings due to stray current are eliminated. The potential difference between the reference electrode and the glass pH electrode in the pH sensor is dependent upon the pH of the measured anolyte effluent stream. The difference between these potentials, through the use of the Nernst Equation, permits the pH of the anolyte effluent stream to be determined.

Under operating conditions encountered in filter press membrane chloralkali type of electrolytic cells, the pH sensor using a reference electrode with a porous polytetrafluoroethylene membrane can operate for extended periods in pH ranges of from about 2 to about 3. On a short term basis of approximately 10 to 15 hours, pH readings as high as about 12 have been monitored. In a flow loop pattern such as that disclosed herein, pH sensors such as sensor 14 have been employed in temperature ranges from about 25° C. to about 100° C.

The pH sensor employed is manufactured by Innovative Sensors, Inc. of Anaheim, Ca., and uses a glass pH electrode and a reference electrode with a porous polytetrafluoroethylene membrane. The porous polytetrafluoroethylene membrane uses a material sold under the trademark of Teflon ® by E. I. DuPont de Nemours & Co. of Wilmington, Delaware. The membrane is actually in the form of an annular seal that is anion selectively permeable to permit chlorine ions to pass through the membrane about the central pH glass electrode or probe. This selective passage of the chlorine ions permits the slight millivolt differential between the potential of the reference electrode and the potential of the glass electrode within the probe or pH sensor 14 to then be measured. The reference electrode is typically comprised of a plurality of silver/silver chloride leads embedded in the porous polytetrafluoroethylene membrane. The glass pH electrode uses a standard pH responsive glass with very high electrical resistance.

The value of employing an electrometric pH probe in a flow loop such as that shown to continuously monitor anolyte pH can be seen where membranes or separators are employed in chloralkaki cells, for example, which require a relatively narrow pH range of electrolyte for optimum or safe operation. Since the pH sensor 14 is connected to external pH circuitry to monitor the pH during operation, should the pH of the electrolyte be above the desired level, it can be quickly detected. The pH can then be adjusted by the addition of predetermined amounts of an appropriate acid to reduce the pH to the desired level either manually or by automatic pH control apparatus.

pH sensors 14 employing a reference electrode with a porous polytetrafluoroethylene membrane or plug seal are particularly useful in the method of monitoring electrolyte or brine pH in electrolytic cells, such as filter press membrane chloralkali cells, because the entire membrane surface provides a porous junction in contact with the electrolyte solution to permit the desired anions, typically chlorine ions, to pass through. This obviates the need for a flowing liquid junction to keep the electrolyte solution from contaminating the reference solution, since the electrolyte solution being monitored is the reference solution. The porous polytetrafluoroethylene membrane or plug seal also obviates the problem of gas bubble blockage that is typically encountered in gas generating electrolytic cells. Lastly, in the type of flow loop disclosed herein, the pH sensor with a reference electrode having a porous polytetrafluoroethylene membrane provides greater reliability over an extended period of time in its pH readings because of the electrolyte being the reference solution.

The flow loop disclosed herein also facilitates acclimation of the pH sensor 14 during initial start-up of the pH monitoring system. As previously mentioned, the wetting solution in the pH sensor 14 is replaced over a predetermined period of time, generally from about 1 to about 3 hours, by diffusion of the electrolyte being monitored, in this case the spent brine, into the polytetrafluoroethylene plug seal or membrane material to become the reference electrolyte. This acclimation is accomplished by installing the pH sensor 14 in the by-pass loop 15 and then opening shut-off valves 16 and 18 to fill the loop with the anolyte effluent or spent brine. Shut-off valve 19 is temporarily closed. When the by-pass loop 15 is filled, the valves 16 and 18 may be closed and valve 19 reopened, or the system may continue to flow to permit the spent brine to flow through the by-pass loop 16. In either event, the pH sensor 14 is exposed to the spent brine so that it may replace the wetting solution and a predictable and steady reference potential will be established prior to initiation of monitoring the electrolyte's pH. The acclimation period prior to obtaining reliable readings may be less where the pH sensor 14 is used in the electrolyte of a chlorate cell because of the more neutral nature of the electrolyte encountered.

While the preferred structure in which the principles of the present invention have been incorporated is shown and described above, it is to be understood that the invention is not to be limited to the particular details thus presented, but, in fact, widely different means and methods may be employed in the practice of the broader aspects of this invention. For example, it is possible that a pH sensor employing a reference electrode with a porous polytetrafluoroethylene membrane could be employed in a flow loop for application in dechlorination towers in chloralkali plants prior to the brine being resaturated. Also, any material which is anion selectively porous could be used as the membrane material. The scope of the appended claims is intended to encompass all obvious changes in the details, materials, and arrangements of parts and the method disclosed which will occur to one of skill in the art upon a reading of this disclosure.

Having thus described the invention, what is claimed is:

1. A method of electrometrically monitoring the pH of the cell electrolyte in a chloralkali electrolytic cell with a pH sensor initially moistened by a wetting solution, the pH sensor further having a reference electrode with a porous polytetrafluoroethylene membrane comprising the steps of:
   (a) placing the pH sensor in an electrolyte flow stream so that the membrane is constantly wetted with electrolyte;
   (b) using the cell electrolyte as the reference electrolyte by having the wetting solution replaced by diffusion of the cell electrolyte into the membrane during an acclimation period;
   (c) connecting the pH sensor to a potential measuring instrument;
   (d) leaving the pH sensor ungrounded; and
   (e) letting the reference electrode fluctuate with the electrical potential of the electrolyte flow stream.

2. The method according to claim 1 further comprising acclimating the pH probe for a predetermined period in the electrolyte to displace any wetting solution adjacent the reference electrode and to establish a steady reference potential.

3. The method according to claim 1 further comprising placing the pH sensor in an anolyte effluent flow stream external of the electrolytic cell.

4. The method according to claim 3 further comprising providing a siphon break in the anolyte effluent flow stream between the electrolytic cell and the pH sensor.

5. The method according to claim 3 further comprising placing the pH sensor in the anolyte flow stream of a filter press membrane type of electrolytic cell.

6. The method according to claim 3 further comprising placing the pH sensor in the anolyte flow stream of a diaphragm type of electrolytic cell.

7. The method according to claim 1 further comprising placing the pH sensor at the low point in a flow loop of the anolyte flow stream with a level of electrolyte at the low point sufficient to keep at least the porous polytetrafluoroethylene membrane of the reference electrode immersed therein.

8. The method according to claim 1 further comprising adjusting the pH of the electrolyte in response to the readings obtained from the pH sensor by the selective addition of acid to the electrolyte to maintain the pH of the electrolyte within a predetermined range.

9. The method according to claim 1 further comprising placing the pH sensor in the anolyte flow stream of a filter press membrane type of electrolytic cell.

10. The method according to claim 1 further comprising placing the pH sensor in the anolyte flow stream of a diaphragm type of electrolytic cell.

11. The method according to claim 1 wherein the method of monitoring is employed in an electrolytic cell producing chlorate.

12. The method according to claim 1 wherein the method of monitoring is employed in an electrolytic cell producing alkali metal hydroxide and a halogen gas product.

* * * * *